US008900570B2

(12) United States Patent
Israelsen

(10) Patent No.: US 8,900,570 B2
(45) Date of Patent: *Dec. 2, 2014

(54) TREATMENT OF IBD AND IBS USING BOTH PROBIOTIC BACTERIA AND FERMENTED CEREAL AS TREATMENT EFFECTORS

(71) Applicant: Nordisk Rebalance A/S, Allerod (DK)

(72) Inventor: Hans Israelsen, Allerod (DK)

(73) Assignee: Nordisk Rebalance A/S, Allerod (DK)

( * ) Notice: Subject to any disclaimer, the term of this patent is extended or adjusted under 35 U.S.C. 154(b) by 134 days.

This patent is subject to a terminal disclaimer.

(21) Appl. No.: 13/826,076

(22) Filed: Mar. 14, 2013

(65) Prior Publication Data

US 2013/0209404 A1    Aug. 15, 2013

Related U.S. Application Data

(60) Continuation of application No. 13/540,827, filed on Jul. 3, 2012, now Pat. No. 8,846,029, which is a division of application No. 12/066,246, filed as application No. PCT/DK2006/000526 on Sep. 27, 2006, now abandoned.

(60) Provisional application No. 60/744,717, filed on Apr. 12, 2006, provisional application No. 60/721,276, filed on Sep. 28, 2005.

(30) Foreign Application Priority Data

Sep. 28, 2005   (EP) ................................ 05388079
Apr. 12, 2006   (DK) ............................... 200600529

(51) Int. Cl.

| | | |
|---|---|---|
| A01N 63/00 | (2006.01) | |
| C12N 1/20 | (2006.01) | |
| A61K 35/66 | (2006.01) | |
| A61K 31/685 | (2006.01) | |
| A61K 35/74 | (2006.01) | |
| A61K 45/06 | (2006.01) | |
| A23L 1/30 | (2006.01) | |
| A23L 1/172 | (2006.01) | |
| A61K 36/899 | (2006.01) | |

(52) U.S. Cl.
CPC ............ *A61K 35/66* (2013.01); *A61K 31/685* (2013.01); *A61K 35/74* (2013.01); *A61K 35/745* (2013.01); *A61K 35/747* (2013.01); *A61K 45/06* (2013.01); *A23L 1/3014* (2013.01); *A23L 1/172* (2013.01); *A61K 35/744* (2013.01); *A61K 36/899* (2013.01); *A61K 35/742* (2013.01); *A23V 2002/00* (2013.01); *A23V 2200/3204* (2013.01)
USPC ................................. 424/93.45; 435/252.9

(58) Field of Classification Search
None
See application file for complete search history.

(56) References Cited

U.S. PATENT DOCUMENTS

| | | | |
|---|---|---|---|
| 5,190,755 | A | 3/1993 | Molin et al. |
| 5,474,932 | A | 12/1995 | Bengmark et al. |
| 5,587,314 | A | 12/1996 | Bengmark et al. |
| 5,591,428 | A | 1/1997 | Bengmark et al. |
| 6,159,465 | A | 12/2000 | Adlerberth et al. |
| 6,537,544 | B1 | 3/2003 | Johansson et al. |
| 7,220,409 | B2 | 5/2007 | Norman et al. |
| 7,311,932 | B1 | 12/2007 | Berggren et al. |
| 2004/0028667 | A1 | 2/2004 | Norman et al. |
| 2004/0048356 | A1 | 3/2004 | Johansson et al. |

FOREIGN PATENT DOCUMENTS

| | | |
|---|---|---|
| DE | 10042825 A1 | 3/2002 |
| DE | 10219684 A1 | 11/2002 |
| DE | 10258129 A1 | 6/2004 |
| EP | 0199535 A2 | 10/1986 |
| EP | 0199535 A3 | 10/1986 |
| EP | 0271364 A2 | 6/1988 |
| EP | 0271364 A3 | 6/1988 |
| EP | 414941 A1 | 3/1991 |
| EP | 0199535 B1 | 1/1992 |
| EP | 0271364 B1 | 9/1992 |
| EP | 554418 A1 | 8/1993 |
| EP | 0199535 B2 | 11/1995 |
| WO | WO89/05849 A1 | 6/1989 |
| WO | WO89/08405 A1 | 9/1989 |
| WO | WO91/05850 A1 | 5/1991 |
| WO | WO91/05851 A1 | 5/1991 |
| WO | WO9117672 A1 | 11/1991 |
| WO | WO9301823 A1 | 2/1993 |
| WO | WO9629083 A1 | 9/1996 |
| WO | WO9918188 A1 | 4/1999 |
| WO | WO0070972 A1 | 11/2000 |
| WO | WO01/70246 A1 | 9/2001 |
| WO | WO0218442 A1 | 3/2002 |

(Continued)

OTHER PUBLICATIONS

Ahrne et al. "Plasmids in *Lactobacillus* Strains Isolated from Meat and Meat Products," System. Appl. Microbiol. vol. 11, pp. 320-323, (1989).

(Continued)

*Primary Examiner* — Jon P Weber
*Assistant Examiner* — Aaron J Kosar
(74) *Attorney, Agent, or Firm* — McLane, Graf, Raulerson & Middleton, PA

(57) ABSTRACT

The invention covers a novel treatment strategy that considerably improves conventional probiotic treatments of inflammatory bowel diseases, irritable bowel syndrome and other gastrointestinal disorders. Both probiotic microorganisms and the carrier of the probiotic microorganisms in form of a fermented cereal gruel are used as treatment effectors. Phospholipids may also be an effector. The novel treatment strategy is capable of removing the symptoms of inflammatory bowel diseases regardless of a mild, moderate or severe stage of the disease.

25 Claims, No Drawings

(56) References Cited

FOREIGN PATENT DOCUMENTS

| WO | WO02/39834 A1 | 5/2002 |
|---|---|---|
| WO | WO02/086136 A1 | 10/2002 |
| WO | WO2004067731 A1 | 8/2004 |
| WO | WO2004087893 A1 | 10/2004 |

OTHER PUBLICATIONS

Cunningham-Rundles et al. "Probiotics and Immune Response," The American Journal of Gastroenterology, vol. 95, No. 1, pp. S22-S25, (2000).

Lidbeck et al. "Impact of *Lactobacillus acidophilus* Supplements on the Human Oropharyngeal and Intestinal Microflora," Scand. J. Infect. Dis vol. 19, No. 5, pp. 531-537, (1987).

Osman et al, "Modulation of the Effect of Dextran Sulfate Sodium-Induced Acute Colitis by the Administration of Different Probiotic Strains of *Lactobacillus* and *Bifidobacterium*," Digestive Diseases and Sciences, vol. 49, No. 2, pp. 320-327 (2004).

Stahl et al. "Restriction Endonuclease Patterns and Multivariate Analysis as a Classification Tool for *Lactobacillus* spp.," International Journal of Systematic Bacteriology, vol. 40, No. 2, pp. 189-192, (1990).

Savage "Mechanisms by which indigenous microorganisms colonize gastrointestinal epithelial surfaces," Prog. Food Nutr. Sci, vol. 7, No. 3-4, Abstract Only, (1983).

Blandino et al. "Cereal-based fermented foods and beverages," Food Research International vol. 36, pp. 527-543, (2003).

Opere et al. "In Vivo Evaluation of *Lactobacillus* Species as Probiotics in the Control of Shigellosis in Infants," Advances in Food Sciences, vol. 25, No. 3, pp. 112 to 116 (2003).

Olukoya et al. "Production of DogiK: an Improved Ogi (Nigerian Fermented Weaning Food) with Potentials for Use in Diarrhoea Control," Journal of Tropical Pediatrics, vol. 40, No. 2, pp. 108-113 (1994) (Abstract only).

Rani et al. "Probiotic fermented food mixtures: possible applications in clinical anti-diarrhoea usage," Nutrition and Health, vol. 12, No. 2, pp. 97-105(1998) (Abstract only).

Bengmark, "Synbiotic Control of Inflammation and Infection in Transplantation", Transplantation Reviews, 2004; 18 (1): 38-53.

Bengmark and Martindale, "Prebiotics and Synbiotics in Clinical Medicine", Nutrition in Clinical Practice, 2005; 20: 244-261.

Bibiloni et al.,"VSL #3 Probiotic-Mixture Induces Remission in Patients with Active Ulcerative Colitis" American Journal of Gastroenterology, 2005; 100:1539-1546.

Backhed et al., "Host-Bacterial Mutualism in the Human Intestine", Science, 2005; 307: 1915-1920.

Christensen et al., "Lactobacilli Differentially Modulate Expression of Cytokines and Maturation Surface Markers in Murine Dendritic Cells," J Immunol, 2002; 168: 171-178.

Goossens et al., "Survival of the probiotic, *L. plantarum* 299v and its effects on the faecal bacteria flora, with and without gastric acid inhibition", Digestive and Liver Disease, 2005; 37(1): 44-50.

Guslandi et al., "A pilot trial of *Saccharomyces boulardii* in ucerative colitis" Eur. J. Gastroenterol Hepatol., 2003; 15 (6): 697-608.

Ishikawa et al., "Randomized Controlled Trial of the Effect of Bifidobacteria-Fermented Milk on Ulcerative Colitis" Journal of the American College of Nutrition, 2002; 22(1): 56-63.

Johansson et al., "Administration of Different *Lactobacillus* Strains in Fermented Oatmeal Soup: In Vivo Colonization of Human Intestinal Mucosa and Effect on the Indigenous Flora", Applied and Enviromental Microbiology, 1993; 59(1): 15-20.

Kim et al., "A randomized controlled trial of a probiotic VSL#3, on gut transit and symptoms in diarrhoea-predominat irritable bowel syndrome", Aliment Pharmacol Ther., 2003; 17: 895-904.

Kruis et al., "Mantaining remission of ulcerative colitis with the probiotic *Escherichia coli* Nissle 1917 is as effective as with standard mesalazine", GUT, 2004; 53: 1617-1623.

Mao et al., "The Effects of *Lactobacillus* Strains and Oat Fiber on Methotrexate-Induced Enterocolitis in Rats", Gastroenterology, 1996; 111(2): 334-344.

Meroth et al., "Characterisation of the Microbiotica of Rice Sourdoughs and Description of *Lactobacillus spicheri* sp. nov.", Systematic and Applied Microbiology, 2004; 27: 151-159.

Molin, "Probiotics in foods not containing milk or milk constituents, with special reference to *Lactobacillus plantarum* 299v1-3", Am. J. Clin. Nutr. 2001; 73(2s): 380S-385S.

Niedzielin et al., "A controlled, double-blind, randomized study on the efficacy of *Lacotbacillus plantarum* 299V in patients with irritable bowel syndrome", Eur. J. Gastroenterol Hepatol., 2001;13: 1143-1147.

Nobaek et al., "Alteration of Intestinal Microflora is Associated With Reduction in Abdominal Bloating and Pain in Patients With Irritable Bowel Syndrome", American Journal of Gastroenterology, 2000; 95(5): 1231-1238.

Prantera et al., "Ineffectiveness of probiotics in preventing recurrence after curative resection for Crohn's disease: a randomised controlled trial with *Lactobacillus* GG", GUT, 2002, 51: 405-409.

Schultz et al.,"Rationale for Probiotic and Antibiotic Treatment Strategies in Inflammatory Bowel Diseases", Digestive Diseases, 2003; 21: 105-128.

Sen et al., "Effect of *Lactobacillus plantarum* 299v on Colonic Fermentation and Symptoms of Irritable Bowel Syndrome", Digestive Diseases and Sciences, 2002; 47(11): 2615-2620.

Kato et al., "Randomized placebo-controlled trial assessing the effect of bifidobacteria-fermented milk on active ulceratice collitis" Aliment Pharmacol Ther. 2004; 20: 1133-1141.

Rutgeerts et al., "Optimizing Anti-TNF Treatment in Inflammatory Bowel Disease," Gastroenterology, 2004, 126 1593-1610.

Costello et al., "Dissection of the Inflammatory Bowel Disease Transcriptome Using Genome-Wide cDNA Microarrays," PLoS Medicine, 2005; 2(8): e199.

Stremmel, et al., "Retarded release phosphatidylcholine benefits patients with chronic active ulcerative colitis," GUT Jul. 2005; 54(7) pp. 966-971.

Bengmark, Stig. "Immunonutrition: Role of Biosurfactants, Fiber, and Probiotic Bacteria" Nutrition 1998, 14(7/8), pp. 585-594.

Kennedy et al., Probiotic Therapy Fails to Improve Gut Permeability in a Hapten Model of Colitis,: Scand J Gasteroenterol, Dec. 1, 2000, 12, pp. 1266-1271.

International Search Report, dated Jan. 15, 2007, which issued during the prosecution of International Application No. PCT/DK2006/000526 and a European Search Report dated Dec. 21, 2005, which issued during the prosecution of EP 05 38 8079, 5 pages.

Jonkers, D. and Stockbrugger, R. "Probiotics and inflammatory Bowel Disease," J R Soc Med. Apr. 2003; 96(4): 167-171.

DSMZ "*Lactobacillus plantarum*" DSMZ catalogue, accessed online <URL:http://www.dsmz.de/catalogues/catalogue-microorganisms.html#searchResult> retrieved Aug. 27, 2012, 2 pages.

Stremmel W. et al., "Phosphatidylcholine for Steroid-Refractory Chronic Ulcerative Colitis:", Annals of Internal Medicine, 147(9): 603-610, 2007.

Stremmel W. et al., "Phosphatidylcholine (Lecithin) and the Mucus Layer: Evidence of Therapteutic Efficacy in Ulcerative Colitis?" Digestive Diseases, 28: 490-496, 2010.

Stremmel W. et al., "Delayed Release Phosphatidylcholine as New Therapeutic Drug for Ulcerative Colitis—a Review of Three Clinical Trials", Expert Opin. Investig. Drugs, 19(12), pp. 1623-1630, 2010.

Harlow, Brittany E., "Changes to the Equine Hindgut Microflora in Response to Antibiotic Challenge", Thesis and Dissertions—Animal and Food Sciences, Univerisity of Kentucky, Chap. 5, pp. 115-126, 2012. uknowledge.uky.edu/animalsci_etds/12.

TREATMENT OF IBD AND IBS USING BOTH PROBIOTIC BACTERIA AND FERMENTED CEREAL AS TREATMENT EFFECTORS

FIELD OF THE INVENTION

The present invention relates to the treatment and maintenance treatment of inflammatory bowel diseases (IBD) and inflammatory bowel syndrome (IBS). In particular, it concerns the use of both fermented cereals and probiotic, preferably anti-inflammatory, microorganisms as treatment effectors for combating IBD and IBS in a novel treatment concept. The invention further concerns the use of phospholipid as a third treatment effector.

BACKGROUND OF THE INVENTION

Ulcerative colitis (UC) and Crohn's Disease (CD) are inflammatory bowel diseases (IBD) characterized by chronic inflammation in the intestines. UC occurs in the colon while CD may be present in the entire gastrointestinal (GI) tract. The clinical symptoms are diarrhea, abdominal pain, occasional rectal bleeding, weight loss, tiredness and sometimes fever. Although occurring at any age, IBD is most common in teenagers and young adults, which consequently may suffer from delayed development and stunted growth. The frequency of the disease is similar to type 1 diabetes in Europe and the USA. The clinical course of IBD varies considerably. Patients with mild to moderate symptoms may be treated without hospitalization. However, 10-15% of patients experience a severe course of the disease, which in many cases is followed by surgery.

IBD is treated medically by reducing the inflammation and thereby controlling the gastrointestinal symptoms. However, there is currently no medical cure for IBD. Colonectomy may eliminate UC but reduces life quality and increases the risk of complications. The available medical treatments include the use of 5-aminosalicylic acid (5 ASA), corticosteroids and immunomodulatory medicaments. Prolonged treatment of mild to moderate IBD symptoms is usually carried out using 5 ASA while corticosteroids and immunomodulatory medicaments are used to treat severe symptoms. Diarrhea or abdominal pain appear as side effects of 5 ASA whereas long term use of corticosteroids frequently shows serious side effects including reduction in bone mass, infection, diabetes, muscle wasting and psychiatric disturbances. Immunomodulatory medicaments suppress the immune system, which controls the IBD symptoms. However, the resulting immunocompromised state leaves the patient susceptible to many diseases.

IBD seems to be a result of an uncontrolled cascade in the immune response. The successful treatment of CD patients with antibodies against the pro-inflammatory cytokine TNF-α supports this assumption (Rutgeerts et al. 2004 Gastroenterology 126:1593-610). However, a prolonged antibody treatment will result in a general lowering of the TNF-α level, which eventually will lead to susceptibility to other diseases.

The reason for the chronic uncontrolled immune response in IBD has not been established. However, both genetic dispositions and the composition of the microbial flora residing in the intestinal tract of the patient are putative causes. Recently it has been reported that several hundred genes may be involved in a genetic disposition for IBD (Costello et al. 2005 PLoS Med 2(8): e199), which makes the development of a successful treatments through genetic strategies extremely difficult. Although it was found that *Helicobacter pylori* is the cause for peptic ulcer disease, no specific pathogens have been found to be the cause of IBD. However, it is generally believed that the commensal microorganisms in the GI tract are key factors in the exaggerated immune response in IBD patients (Schultz et al. 2003 Dig. Dis. 21: 105-128).

In vitro tests have shown that immune competent cells react differently upon contact to different bacteria (Christensen et al. 2002 J. Immunol. 168:171-8). Bone marrow-derived dendritic cells (DC) are exposed to microbial strains and following the cytokines produced by the DC are determined. Predominant production of proinflammatory interleukins such as IL 6, IL12 and TNFα indicates a proinflammatory response upon exposure to a microbial strain. In contrast, a predominant secretion of anti-inflammatory interleukins such as IL4 and IL10 indicates an anti-inflammatory response upon the exposure. In general, microorganisms can be divided into two groups inducing pro-inflammatory or anti-inflammatory cytokines, respectively. In the following, such microorganisms are termed "pro-inflammatory" and "anti-inflammatory" microorganisms, respectively.

Irritable Bowel Syndrome (IBS) is part of a spectrum of diseases known as functional gastrointestinal disorders which include diseases such as non-cardiac chest pain, non-ulcer dyspepsia, and chronic constipation or diarrhea. These diseases are all characterized by chronic or recurrent gastrointestinal symptoms for which no structural or biochemical cause can be found. Patients suffering from IBD and IBS share several kinds of symptoms.

In 1907, the inventor of the modern immunology Elias Metchnikoff suggested that some intestinal bacteria have a beneficial role on the health. Today, these bacteria are termed probiotics defined as live microorganisms which administered in adequate amounts confer a beneficial health effect on the host.

A long range of effects have been postulated for instance that probiotics can help reduce the risk of certain diarrheal illnesses, improve the immune function, reduce the risk of cancer and cardiovascular diseases, assist lactose intolerant people etc. Some of the postulated effects have been investigated scientifically during the last two decades. In particular, research has been intense on the treatment of gastrointestinal diseases using probiotics. The rationale is that changing the microflora in the GI tract of IBD and IBS patients may reduce the immune aggressiveness thereby relieving the symptoms.

Today, three basic approaches exist for changing the microflora of the intestine, namely the use of i) antibiotics, ii) probiotics, and iii) synbiotics. The administration of antibiotics kills a subpopulation of the microflora while probiotics—if administered in appropriate amounts—are thought to displace some of the existing microorganisms in the intestine. Antibiotics and probiotics have also been used in combination. Synbiotics are mixtures of probiotics and substances—socalled prebiotics—that provide a substrate to specifically stimulate the growth of the probiotic microorganisms. None of these approaches—alone or in combination—have proven to be competent concerning a clear and a long term reduction of IBD or IBS symptoms.

Several strains of Lactic Acid Bacteria and species from the genus *Bifidobacterium* are probiotic, which implies that they one way or another have been shown to promote a specific health effect. Human clinical trials using probiotics alone or in combination with antibiotics have been performed to identify strains and/or formulations for the treatment of patients with IBD or IBS symptoms or for keeping already treated IBD patients in remission.

WO96/29083 and EP 554418 disclose three intestine colonizing *lactobacillus* strains including the two *Lactobacillus*

*plantarum* strains 299 (DSM 6595) and 299v (DSM 9843) and *Lactobacillus casei* ssp. *rhamnosus* 271 (DSM 6594) which may be fermented in oat gruel. It is speculated that these strains may be used to treat IBS. EP 415941 discloses methods for preparing nutrient composition comprising treatment of oat gruel with enzymes before mixing with lactobacilli The results from trials with *Lactobacillus plantarum* strains 299v administered in a daily total amount of up to $2 \times 10^{10}$ colony forming units (cfu) in a fruit drink are ambiguous since some positive effects on IBS patients are reported in two studies (Nobaek et al. 2000 Am J. Gastroenterol. 95:1231-8 and Niedzielin et al. 2001 Eur J Gastroenterol Hepatol. 13:1143-7) while a later study using the same strain showed no effect on the IBS patients (Sen et al. 2002 Dig Dis Sci 47:2615-20).

Other species of *Lactobacillus* have been tested as for instance *Lactobacillus* rhamnosus GG, which was administered in an amount of $6 \times 10^9$ bacteria twice a day for 52 weeks in a double blinded RCT study for preventing recurrence after curative resection for Crohn's disease (Prantera et al 2002 Gut 51:405-409). This study showed that the probiotic treatment had no effect compared to placebo.

Another strategy has been to use a combination of different probiotic strains, of which one product is called VSL#3. It consists of eight different bacterial strains and is administered as capsules possibly with freeze or spray dried bacteria. A recent study was performed with the administration to UC patients of $1.8 \times 10^{12}$ VSL#3 bacteria twice a day for six weeks (Bibiloni et al. 2005 American Journal of Gastroenterology 100:1539-46). The patients had mild to moderate UC symptoms and the study was performed as an open study without placebo. Remission was achieved in 53% of patients.

In another study, 250 mg of the yeast *Saccharomyces boulardii* was administered three times a day for four weeks. Remission was obtained in 71% of the 17 UC patients (Guslandi et al. 2003 Eur J Gastroenterol Hepatol. 15:697-8). These results have not been confirmed in controlled studies.

A RCT study on maintaining remission of UC was performed recently using the *E. coli* Nissle strain (Kruis et al. 2004 Gut 53:1617-23).

Kato et al. (2004 Aliment Pharmacol Ther. 20:1133-41) and Ishikawa et al. (2003 J Am Coll Nutr. 22:56-63) have disclosed controlled trials assessing the effect of bifidobacteria-fermented milk on ulcerative colitis.

The number of microorganisms in the GI tract is approximately $10^{14}$ (Backhed et al. 2005 Science 307:1915-20). As mentioned previously, the results from clinical trials have shown that administration of large amount of probiotics may have a positive effect on the IBD symptoms. However, administration to IBD patients of more than $10^{12}$ VSL#3 microorganisms each day for several weeks led to the identification of only small amounts of only two of the provided eight strains in biopsies from the patients (Bibiloni et al. 2005 American Journal of Gastroenterology 100:1539-46). No dramatic change in the composition of the microflora was observed.

Hitherto, the general assumption in the scientific community concerning the treatment of IBD and IBS is that probiotics have shown some promising results but are not sufficient effective (Schultz et al. 2003 Dig. Dis. 21:105-28 and Kim et al. 2003 Aliment Pharmacol Ther. 17:895-904).

In summary, the current applied strategies for treating IBD or IBS using probiotics aiming to change the composition of the GI microflora cover—alone or in combination—i) oral administration of different amounts of probiotic microorganisms also including concomitant administration of conventional medicines like 5 ASA, ii) oral administration of substrates specifically favourable to the growth of probiotic microorganisms, iii) short term oral administration of antibiotics and iv) the use of probiotic microorganisms capable of transiently colonizing the intestine and/or producing compounds that are toxic to other bacterial species. These strategies have not proven to be sufficiently effective neither in reducing the symptoms experienced by IBD and IBS patients nor changing the composition of the microflora in the intestines.

Recently, it has been reported that a randomized controlled trial (RCT) comprising a three months treatment of UC patients with retarded release of phosphatidylcholine (PC) in the colon has shown a remission in 53% of the patients (Stremmel et al. 2005 Gut 54:966-971).

DISCLOSURE OF THE INVENTION

Summary of the Invention

The previously described treatments of gastrointestinal disease such as IBD and IBS using probiotics have not proven sufficiently beneficial and therefore need to be improved in order to be a serious supplement or even an alternative to traditional treatment with chemical substances. One of the factors which distinguish the present invention from the previously disclosed use of probiotics in treating gastrointestinal diseases is the use of high amounts of supplementary effectors combined with relatively high amounts of the probiotics.

In one aspect, the present invention is thus based on the discovery that a combined high intake of fermented oat gruel and high intake of probiotic microorganisms by IBD and IBS patients provides a surprising improvement over the previously described results obtained with probiotic microorganisms. In the prior art the probiotic bacteria were used in high amounts alone or in lower amounts in what is considered to be with respect to the disease inert carriers such as fermented oatmeal or milk.

It has been realised during the development of the present invention that fermented cereal can play an important active role in combating inflammatory disorders in the intestines most likely caused by pro-inflammatory microorganisms, and should therefore be used in an amount higher than previously taught. In the prior art fermented cereal (oat gruel) was merely considered to be a growth medium and carrier of the probiotics. The fermented cereal has not previously been used in high amounts in the treatment of IBD and IBS patients and nothing in the prior art suggests that fermented cereals may play an important role in such a treatment.

In another aspect of the invention the addition of the phospholipids, phosphatidylcholine (PC), lysophosphatidylcholine (LPC), phosphatidylinositol (PI) and/or phosphatidylethanolamine (PE) can be additionally beneficial in the treatment of IBD and IBS patients, especially patients with a sub-optimal mucus layer in the intestines.

Mucus constitutes a physical barrier to the epithelial cells of the intestine and seems to be important in the balanced contact between microorganisms and the surface cells of the GI tract. Phospholipids are important components of the intestinal mucus. Phospholipids in the mucus consist mainly of phosphatidylcholine and lysophosphatidylcholine, but also phosphatidylinositol and phosphatidylethanolamine. PC seems to play a major role in the so called mucosal defense by establishing a protective hydrophobic surface. It has been shown that phosphatidylcholine and phosphatidylinositol have a therapeutic effect on the development of acetic acid-induced colitis in rats (Fabia et al. 1992 Digestion 53:35-44). The content of PC and LPC in the colonic mucus of patients with UC is significant lower compared to healthy controls (Ehehalt et al. 2004). Peripheral blood leucocytes from patients with Crohn's disease have abnormal essential fatty acid metabolism apparently correlated to the zinc content (Cunnane et al. 1986) and membranes of erythrocytes from patients with Crohn's disease have a significant increase of sphingomyelin and a decrease of phosphatidylcholine (Aozaki 1989).

Phosphatidylcholine, for example in the form of commercially available lechitins (which also contains amounts of LPC, PI and PE) is the preferred phospholipids to be added to the fermented product. Although it has been shown that certain probiotic bacteria may induce the production of mucus in the intestine (Mack et al. 1999), combining probiotics with phospholipids that specifically support building up a functional intestinal mucus has not been suggested previously.

In a further aspect of the present invention it has been realised that in order to secure a beneficial effect of the fermented cereal and the probiotic microorganisms, intake of substances which disturb the desired effect should be avoided during the treatment. Such substances may promote the growth of intestinal pro-inflammatory microorganisms present in the patients before and during the treatment or stimulate immunological reactions in the intestines, which is unfavourable to the medical treatment. Examples of such harmful substances are easily fermentable sugars present in e.g. fruit drinks, fruit pulp, dried or processed fruit and the like and milk and milk products.

The present invention thus concerns the use of i) high doses of a fermented cereal and ii) high doses of probiotic microorganisms in a novel treatment strategy that considerably improves the conventional probiotic treatments of IBD and IBS patients. The fermented cereal negatively change the growth and life maintenance conditions for the residing microorganisms in the intestine of IBD and IBS patient while the supply of probiotics provides anti-inflammatory inducing microorganisms to displace pro-inflammatory inducing microorganisms from the original microflora, which have less favourable conditions in the fermented cereal. The probiotic microorganisms are adapted to the environment in the fermented cereal composition prior to administration to the patients. In addition, phospholipids, in particular phosphatidylcholine and lysophosphatidylcholine may be used to further improve the treatment effect by building up or strengthen the functional mucus layer in the intestines. The novel treatment strategy may be applied alone or in combination with the administration of conventional medicines like 5 ASA and corticosteroids.

The novel concept for the treatment or the maintenance treatment of IBD, IBD related diseases and IBS includes the administration of an efficient amount of fermented cereal together with an efficient amount of probiotic microorganisms and optionally phospholipids. The probiotic microorganisms are non-pathogenic microorganisms, preferably anti-inflammatory microorganisms. The cereal may be any suitable cereal which is fermentable by suitable non-pathogenic microorganisms and in its fermented state usable as an active effector. The probiotic microorganisms in the ready-to-use product may be the cereal-fermenting microorganisms per se. However, the probiotic microorganisms in the ready-to-use product may also be other non-pathogenic, preferably anti-inflammatory microorganisms that are added to the fermented cereal composition. In the later case the cereal-fermenting microorganisms may be alive or dead in the ready-to-use product. The phospholipids may preferably be commercially available lecithin—from soy beans—containing at least 20% PC.

A daily intake of an efficient amount of a fermented cereal composition consisting of at least 10 grams dry weight of a fermented cereal—for example fermented oat gruel—and at least $5 \times 10^{10}$ colony forming units (cfu) of probiotic microorganisms—for example lactic acid bacteria such as intestine colonizing *Lactobacillus* or *Bifidobacterium* spp. The preferred amount per day is at least 18 g dry weight of fermented cereal, e.g. fermented oat gruel and $1 \times 10^{11}$ cfu of probiotic microorganisms, and more preferred 36 g dry weight of fermented cereal, e.g. fermented oat gruel and $2 \times 10^{11}$ cfu of probiotic microorganisms. In another preferred embodiment, the daily intake is about 90 g dry weight of fermented cereal e.g. fermented oat gruel and about $5 \times 10^{11}$ cfu of probiotic microorganisms such as intestine colonizing *Lactobacillus* spp. Larger amounts of fermented cereal e.g. fermented oat gruel and numbers of colony forming units of probiotic microorganisms may be used if desired (and accepted by the patient). Preferably the daily intake is divided into two or more intakes. The first intake of the ready-to-use product is preferably before breakfast and the last intake is preferably after the last meal and drink of the day. The last intake is chosen to allow the amount of fermented cereal and microorganisms to be present in the intestine as long as possible without being "diluted" by "normal" foods and drinks, which may contain easy fermentable substrates. It is acceptable to drink water after the last intake. Intake of the ready-to-use product in connection with each meal during the day may also be an option.

When phospholipids are a part of the treatment regime, the daily intake is at least 0.1 g phophatidylcholine, preferably more than 0.5 g and most preferably more than 1 g per day. The phospholipids may be added as a commercial lecithin product. When using the ready to use product without added lecithin, fluctuations between a state of obvious IBD-symptoms and remission have been observed for patients for up to week number 12 in the treatment period. In contrast, treatment with the ready to use product containing added lecithin has shown a more stable remission and in some cases a faster remission during the treatment period.

The probiotic microorganisms are preferably not freeze or spray dried in the ready-to-use product because the microorganisms preferably should be as robust as possible when entering the intestines in order to successfully compete with the pro-inflammatory part of the microflora already present in the intestines. However, some strains may be sufficiently robust and/or some protocols sufficiently gentle to allow spray or freeze dried probiotic microorganisms in the ready-to-use product.

A more efficient treatment or maintenance treatment is obtained if milk products, milk components and easily fermentable sugars such as sucrose, lactose, glucose or fructose are omitted in the ready-to-use product and otherwise avoided in the diet. Accordingly, the ready-to-use product should not comprise any drink containing large amounts of fruit, fruit pulp, dried fruit or similar fruit additives or other energy-providing additives often used in commercial products to enhance taste and nutrition value of the final product. In the same way, large amounts of milk and milk-based additives should not be used in the ready-to-use product. Low- or non-calorie additives may be used in the product for instance to enhance the properties relevant to patient compliance.

The duration of the treatment is dependent on each individual patient and the stage of the disease. The typical treatment periods range from one to 25 weeks but there is no limitation. A continued treatment for a certain period after remission appears to provide better long term effects.

Accordingly the present invention concerns the use of an efficient amount of a fermented cereal composition and an efficient amount of probiotic microorganisms and optionally added phospholipids in the preparation of a medical product for the treatment of a gastrointestinal disease such as IBD, IBD related diseases and IBS.

The cereal is preferably oat, which is fermented by non-pathogenic microorganisms capable of fermenting cereals resulting in a pH below 5.5, Such microorganisms may be lactic acid bacteria, *Propionibacterium* spp and *Bifidobacterium* spp., e.g. one or more *Lactobacillus* spp.

DETAILED DESCRIPTION OF THE INVENTION

IBD is very likely a result of imbalances in the immune system, which may be initiated and preserved by the residing microorganisms of the GI tract including pathogenic or opportunistic pathogenic microorganisms. Attempts to change the flora of microorganisms in the GI tract of IBD or IBS patients have been performed by several scientific groups using probiotic microorganisms and/or antibiotics and/or prebiotics. The previous strategies have covered the administration to patients of large amounts of probiotic microorganisms formulated in capsules (or milk products) or a relative small amount of probiotic microorganisms and fermented oatmeal formulated in fruit drinks. The new strategy presented here, which includes administration of high amounts of both fermented oatmeal and probiotic microorganisms and preferably PC, shows superior results compared to the results presented in the prior art.

The discovery of a positive correlation between a large intake of a product consisting of fermented oatmeal and a *Lactobacillus* strain and the clinical effects as described in Example 2 has successfully been developed into the present invention which offers a surprising novel and advantageous treatment concept for the treatment of IBD, IBS and IBD related diseases. However, the addition of lecithin to the product consisting of fermented oatmeal and a *Lactobacillus* strain has been found to provide an even more advantageous treatment concept with a faster and/or a more stable state of remission obtained within the treatment period as described in Examples 13 and 14. The products used by Nobaek et al. (2000 Am J. Gastroenterol. 95:1231-8) and Niedzielin et al. (2001 Eur J Gastroenterol Hepatol. 13:1143-7) contained a low amount (compared to the present invention) of fermented oatmeal and a *Lactobacillus* strain mixed in a fruit drink. These products lead to insufficient treatment.

The terms used in the present description of the invention are defined below.

The term "inflammatory bowel disease" (IBD) includes ulcerative colitis (UC) and Crohn's disease (CD) that are well characterised diseases. As examples of "IBD-related diseases" may be mentioned collagenous colitis and lymphocytic colitis. Others will be known by the skilled medical doctors.

The term "irritable bowel syndrome" (IBS) is defined as a spectrum of diseases known as functional gastrointestinal disorders which include diseases such as noncardiac chest pain, nonulcer dyspepsia, and chronic constipation or diarrhea. These diseases are all characterized by chronic or recurrent gastrointestinal symptoms for which no structural or biochemical cause can be found. The symptoms are often the same as for IBD patients, except that bleedings do not occur in connection with IBS.

The terms "treatment effector" and "treatment effectors" mean component(s) that exert(s) an effect in reducing IBD and/or IBS symptoms.

The term "cereal" is defined as any plant from the grass family that yields an edible grain (seed). The most common grains are barley, corn, millet, oats, quinoa, rice, rye, sorghum, triticale, wheat and rice. Most preferred is oats. However, suitable parts of alternative plants such as cassava may also be used.

The term "cereal gruel" is defined as cereal grains, flakes, meal, extracts or flour boiled in a liquid, which preferably is water. The cereal gruel is prepared in this way in order to sterilize the suspended cereal and to prepare for the microbial fermentation. Enzymes, compositions containing enzymes and/or appropriate amounts of carbon and energy sources may be added to further prepare for the microbial fermentation and/or provide a desired rheology. By cereal gruel is meant any rheological form of suspended and boiled cereal.

The term "fermented cereal composition" is defined as the resulting product from the growth of one or more non-pathogenic microorganisms on a cereal gruel and containing one or more non-pathogenic microbial strains, which may be dead or alive. Fermented cereal composition is also referred herein as "fermented product" or "fermented oat gruel".

By the term "non-pathogenic microorganisms" is meant any live microbial food or feed supplement that under normal conditions is not harmful to humans or animals.

By the term "cereal-fermenting microorganisms" is meant non-pathogenic microorganisms that are capable of fermenting a cereal resulting in a pH<5.5.

By the term "probiotic microorganisms" is meant non-pathogenic microorganisms that beneficially affect the patient by improving the intestinal microbial balance. Such probiotic microorganisms may preferably be anti-inflammatory microorganisms and/or from the group consisting of Lactic Acid Bacteria and *Bifidobacterium* spp.

Lactic Acid Bacteria are defined as all species, subspecies and strains of the following genera: *Carnobacterium, Enterococcus, Lactobacillus, Lactococcus, Leuconostoc, Oenococcus* and *Pediococcus*. Also covered are non-pathogenic species, subspecies *and* strains of the genus *Streptococcus* such as *Streptococcus salivarius* subsp. *thermophilus* or *Streptococcus thermophilus*.

The term "*Lactobacillus* spp. includes any of the following species: *Lactobacillus acetotolerans, Lactobacillus acidipiscis, Lactobacillus acidophilus, Lactobacillus agilis, Lactobacillus algidus, Lactobacillus alimentarius, Lactobacillus amylolyticus, Lactobacillus amylophilus, Lactobacillus amylovorus, Lactobacillus animalis, Lactobacillus arizonensis, Lactobacillus aviarius, Lactobacillus bifermentans, Lactobacillus brevis, Lactobacillus buchneri, Lactobacillus casei, Lactobacillus coelohominis, Lactobacillus collinoides, Lactobacillus coryniformis* subsp. *coryniformis, Lactobacillus coryniformis* subsp. *torquens, Lactobacillus crispatus, Lactobacillus curvatus, Lactobacillus cypricasei, Lactobacillus delbrueckii* subsp. *bulgaricus, Lactobacillus delbrueckii* subsp *delbrueckii, Lactobacillus delbrueckii* subsp. *lactis, Lactobacillus durianus, Lactobacillus equi, Lactobacillus farciminis, Lactobacillus ferintoshensis, Lactobacillus fermentum, Lactobacillus formicalis, Lactobacillus fructivorans, Lactobacillus frumenti, Lactobacillus fuchuensis, Lactobacillus gallinarum, Lactobacillus gasseri, Lactobacillus graminis, Lactobacillus hamsteri, Lactobacillus helveticus, Lactobacillus helveticus* subsp. *jugurti, Lactobacillus heterohiochii, Lactobacillus hilgardii, Lactobacillus homohiochii, Lactobacillus intestinalis, Lactobacillus japonicus, Lactobacillus jensenii, Lactobacillus johnsonii, Lactobacillus kefiri, Lactobacillus kimchii, Lactobacillus kunkeei, Lactobacillus leichmannii, Lactobacillus letivazi, Lactobacillus lindneri, Lactobacillus malefermentans, Lactobacillus mali,*

*Lactobacillus maltaromicus, Lactobacillus manihotivorans, Lactobacillus mindensis, Lactobacillus mucosae, Lactobacillus murinus, Lactobacillus nagelii, Lactobacillus oris, Lactobacillus panis, Lactobacillus pantheri, Lactobacillus parabuchneri, Lactobacillus paracasei* subsp. *paracasei, Lactobacillus paracasei* subsp. *pseudoplantarum, Lactobacillus paracasei* subsp. *tolerans, Lactobacillus parakefiri, Lactobacillus paralimentarius, Lactobacillus paraplantarum, Lactobacillus pentosus, Lactobacillus perolens, Lactobacillus plantarum, Lactobacillus pontis, Lactobacillus psittaci, Lactobacillus reuteri, Lactobacillus rhamnosus, Lactobacillus ruminis, Lactobacillus sakei, Lactobacillus salivarius, Lactobacillus salivarius* subsp. *salicinius, Lactobacillus salivarius* subsp. *salivarius, Lactobacillus sanfranciscensis, Lactobacillus sharpeae, Lactobacillus suebicus, Lactobacillus thermophilus, Lactobacillus thermotolerans, Lactobacillus vaccinostercus, Lactobacillus vaginalis, Lactobacillus versmoldensis, Lactobacillus vitulinus, Lactobacillus vermiforme, Lactobacillus zeae*. The preferred species is *Lactobacillus plantarum*.

The term "*Bifidobacterium* spp." includes any of the following species: *Bifidobacterium adolescentis, Bifidobacterium aerophilum, Bifidobacterium angulatum, Bifidobacterium animalis, Bifidobacterium asteroides, Bifidobacterium bifidum, Bifidobacterium boum, Bifidobacterium breve, Bifidobacterium catenulatum, Bifidobacterium choerinum, Bifidobacterium coryneforme, Bifidobacterium cuniculi, Bifidobacterium dentium, Bifidobacterium gallicum, Bifidobacterium gallinarum, Bifidobacterium indicum, Bifidobacterium longum, Bifidobacterium longum* by Longum, *Bifidobacterium longum* bv. Infantis, *Bifidobacterium longum* bv. Suis, *Bifidobacterium magnum, Bifidobacterium merycicum, Bifidobacterium minimum, Bifidobacterium pseudocatenulatum, Bifidobacterium pseudolongum, Bifidobacterium pseudolongum* subsp. *globosum, Bifidobacterium pseudolongum* subsp. *pseudolongum, Bifidobacterium psychroaerophilum, Bifidobacterium pullorum, Bifidobacterium ruminantium, Bifidobacterium saeculare, Bifidobacterium scardovii, Bifidobacterium subtile, Bifidobacterium thermoacidophilum, Bifidobacterium thermoacidophilum* subsp. *suis, Bifidobacterium thermophilum, Bifidobacterium urinalis*.

By the term "efficient amount" is to be understood an amount of fermented cereal composition and an amount of one or more probiotic microorganisms to be administered daily to the person to results in a relatively fast reduction of the patient's symptoms. The reduction in symptoms comprises stop of bloody stools and/or at least a 25% reduction in the number of daily stools within seven days from the treatment onset, if the treatment concept is followed. Minor deviation from the present concept may lead to a delay in the reduction of the symptoms. Major deviations may lead to failure of any effect of the treatment.

Oat gruel used in the preparation of the product may be prepared as disclosed in EP 415941. The oat gruel may for example be prepared by using at least 5 g oatmeal per 100 ml liquid or more preferred 10 g oatmeal per 100 ml liquid or even more preferred at least 18 g oatmeal per 100 ml liquid.

The fermented cereal composition is produced by adding an amount of cereal-fermenting microorganisms to the cereal gruel resulting in a pH<5.5 following fermentation at an optimal temperature for at least 12 hours or preferred at least 24 hours.

The term "(ready-to-use) product" is defined as the product to be administered to a patient for instance as a drinkable, eatable, anally administrable or tube administrable product. The ready-to-use product consists of i) a fermented cereal composition, ii) probiotic microorganisms and optionally iii) added phospholipids. Drinkable ready-to-use products may for instance be stored and available in suitable containers. Eatable products may for instance be stored and available in a solid or semi-solid form for example mixed with other eatable ingredients not being contrary to the new treatment concept. Oat biscuits may be an example. Anally administrable ready-to-use products may for instance be in the form of a suppository and tube administrable ready-to-use products may for instance be in a liquid form that is suitable for tube administration via the oral or rectal route.

The cereal-fermenting microorganisms of the fermented cereal composition may per se constitute the probiotic microorganisms in the ready-to-use product. However, the probiotic microorganisms in the ready-to-use product may also be microorganisms that are added to the fermented cereal composition. In the later case the cereal-fermenting microorganisms may be alive or dead in the ready-to-use product. The microorganisms in the fermented cereal composition may be killed for instance by heating the composition before the addition of probiotic microorganism. The appropriate temperature and time depend on the properties of the cereal-fermenting strains. The efficient amount of probiotic bacteria in the ready-to-use product is at least $10^8$ cfu/ml or more preferred at least $10^9$ cfu/ml. Prior to the fermentation, the cereal gruel may be treated with malted flour such as malted barley flour and/or enzyme(s) e.g. amylase or/and added a sufficient amount of energy and carbon source for the growth of the cereal-fermenting microorganisms. Prior to or following the fermentation, the cereal gruel may be treated with enzyme(s) and/or treated physically/mechanically e.g. to reduce the viscosity, to improve the availability of nutrient components, to break down certain cereal molecules, to change the composition of macromolecules and building block molecules, to improve the shelf life or other improvements or modifications. Similarly, the cereal gruel may prior to or following the fermentation be added components to improve or modify the product e.g. by adding phospholipids, proteins, amino acids and/or fibres that for instance may improve the mucus barrier in patients or may improve the transit time of the food in the GI tract.

The term "intestine colonizing" means that a microbial strain must be present transiently or permanently in the intestine upon at least one intake of a sufficient amount of cfu. The analysis for intestine colonizing may be carried out for instance by testing for the presence of a specific strain in the faeces on the days and weeks following the intake. Some strains of *Lactobacillus* spp. may colonize the human intestine for about 14 days.

The terms "one day's treatment", "daily treatment", "daily administration" and "daily intake" are used interchangeably and mean the total dose of the (ready-to-use) product to be taken by or administered to the patient each day in the treatment period. If the treatment is administered by the patient him/herself, the right dose is preferably provided in a suitable container containing the correct dose of the medical product. The total daily dose may advantageously be divided into two or more containers containing the right doses to be taken or administered during the day, for example as the first and the last meal of the day. Alternatively, the patient or the medical staff may measure the right dose for each administration from a larger container comprising the (ready-to-use) product.

The terms "milk products" and "dairy products" mean any product that has been produced from mammal milk and "dairy components" means any component derived, purified or extracted from mammal milk or a dairy product.

The term "easily fermentable sugars" means sugars that constitute an easily accessible source of energy and carbon for microorganisms. Examples of easily fermentable sugars are sucrose, lactose, glucose and fructose. Such sugars are for example present in processed fruits, fruits drinks, dried fruit, marmalades and otherwise treated fruits and should therefore be avoided in the ready-to-use product.

The term "food or medical additives" means any substance that may be added to improve the fermented product in terms of activity towards the gastrointestinal disorder or towards one or more other diseases. Also, "food or medical additives" means any substance that may be added to improve the shelf life, taste, color, or rheological properties of the product. Examples of substances are taste enhancers, colors, pH and osmo-regulators, vitamins, herbs, herbal components, minerals, trace elements, viscosity regulators, lipids, emulsifiers, short chain fatty acids, glutamine and other amino acids, antioxidants, blood pressure regulators, pain relief substances etc. The skilled person would readily know which additives would be suitable. The term minerals comprises pharmaceutical acceptable minerals such as chrome, iron, zinc, copper, calcium, potassium, sodium, manganese and molybdenum. Especially zinc may be added to give a beneficial effect.

The term "lecithin" means both the chemical definition, which is phosphatidylcholine or 1,2-diacyl-glycero-3-phosphocholine, and the commercial definition, which refers to a natural mixture of neutral and polar lipids. Phosphatidylcholine is present in commercial lecithin in concentrations of 20 to 90%. Other components in commercial lechithin are lysophosphatidylcholine, phosphatidylinositol and phosphatidylethanolamine. Most commercial lecithin products contain about 20% phosphatidylcholine. The fatty acids residues of phosphatidylcholine may be saturated, mono-unsaturated or poly-unsaturated. The term "lecithin" also means chemically or commercially defined lecithin in any physical form including liquid, granulated, encapsulated or mixed with any other substances. In particular, the term "lecithin" also means any formulation where lecithin is designed to be released at specific locations in the gastrointestinal tract for instance as defined as "retarded release" by Stremmel et al. 2005 Gut 54:966-971.

The Development of a Novel Concept for the Treatment or Maintenance Treatment of IBD, IBS, and Related Diseases During the development of the novel treatment concept it was speculated how a pronounced clinical effect could be achieved possibly by an efficient change in the composition and/or metabolic activity of the microflora in the intestine. Intake of relatively large amounts of appropriate fermented cereal together with probiotics was surprisingly shown to have an advantageous clinical effect most likely because it is disadvantageous to most of the residing pro-inflammatory inducing microorganisms in the GI tract in terms of substrate for growth and/or life maintenance and advantageous to several probiotic microorganisms in terms of an appropriate environment for life maintenance. In light of the latter aspect, the probiotic microorganisms benefit physiologically if the fermented cereal both constitutes the growth medium for the microorganisms in the production phase and, concomitantly, used as a treatment effector in the medical product. Last but not least, cereals contain a range of components important to man such as carbohydrates, fibres and lipids. Cereals like oats and maize contain relatively large amounts of lipids. It may be speculated that a high amount of polar lipids in cereals may be co-responsible for the positive effects of the novel treatment protocol described here. Accordingly, cereals with a high amount of polar lipids, such as oat, might be preferred. Also, lecithin may be added to the fermented cereal composition to improve the functional properties of the intestinal mucus. Consequently, higher amounts of phospholipids should be added to fermented compositions prepared from cereals with a low content of polar lipids compared to cereals with high amounts of polar lipids.

According to the strategy on efficiently changing the microflora in the GI tract, intake of components that stimulate the growth and maintenance of the residing pro-inflammatory inducing microorganisms should be avoided. Most milk components and sugars like sucrose, lactose, glucose or fructose are easily utilized by bacteria such as *E. coli*. For instance, in competition experiments in flasks most *E. coli* strains would be much faster in utilizing milk components and the sugars mentioned than most lactic acid bacteria or *Bifidobacterium* strains. Therefore, milk products, milk components and easily fermentable sugars should be omitted in the present ready-to-use product and in the treatment or maintenance treatment concept.

The applied probiotic microorganisms should preferably be able—at least transiently—to reside in or colonize the GI tract. Such probiotic microorganisms should also be physiologically robust. There is a long range of probiotic products on the market and many contain freeze or sprayed dried probiotic microorganisms (DDS-Plus® (UAS Lab, MN, USA), VSL#3 (Sigma-Tau, MD, USA), Lp299v (Quest, UK) etc.). Freeze or spray drying usually kills a large percentage of the microorganisms and severely stresses the surviving population (Wang et al. 2004 Int J Food Microbiol. 93:209-17). Although pre-treatment of several microorganisms under mild stress conditions may be beneficial for the survival under future harsh conditions—for instance in the GI tract—, freeze or spray drying is in many cases too rough to result in probiotic microorganisms that are physiologically robust.

One example of the novel concept for the treatment or maintenance treatment of IBD, IBD related diseases and IBS includes the following:

Each day the patient shall drink two or more portions each of 100-250 ml oat gruel fermented with and containing about $10^8$-$10^9$ cfu/ml of one or more intestine colonizing *Lactobacillus* spp, for example *L. plantarum* 299 or *L. plantarum* 299v. The product should preferably contain 12 g lecithin with at least 20% PC per litre fermented oat gruel to obtain a faster remission and or a more stable state of remission during the treatment period. The first intake of fermented oat gruel is performed before breakfast and the last intake preferably performed as the last meal and drink—except for water—of the day. The treatment continues for e.g. 14 weeks.

A more efficient treatment or maintenance treatment is obtained if milk products, milk components and easily fermentable sugars such as sucrose, lactose, glucose or fructose are omitted in the ready-to-use product and avoided in the diet during the treatment period.

The duration of the treatment is dependent on each individual patient and the stage of the disease. The typical treatment periods range from one to 25 weeks but there is no limitation.

The probiotics may be any probiotic microorganisms preferably lactic acid bacteria and/or species from the genus of *Bifidobacterium* and more preferably capable of at least transiently colonizing the intestine. *L. plantarum* 299 and *L. plantarum* 299v are two suitable strains which have been isolated due to their ability to ferment oatmeal and intestine colonizing properties.

As mentioned, there are two reasons for using fermented cereals as a treatment effector. The first is to build up an environment in the GI tract in which the properties for growth or life maintenance for many microorganisms are unfavourable except for selected microorganisms including many probiotics. The second reason is to provide complex lipids, carbohydrates, proteins, fibres and other molecules that may have a positive effect both in providing material for production of physical barriers such as the mucus layer and on the immune system response. The complex lipids, carbohydrates, proteins and other molecules both originate from the oat and probiotics per se but are also an outcome of the fermentation process. The use of added lecithin in the ready-to-use product may provide extra material for the production of an effective intestinal mucus layer. The amount of added lecithin should most likely be higher in the ready-to-use product based on cereals with a low content of phospholipids than in products based on cereals containing relatively large amounts of phospholipids.

Administration of fermented cereal compositions containing probiotic microorganisms and lecithin to IBD and IBS patients for an appropriate period of time will most likely lead to i) a reduced number and/or a reduced metabolic activity in pro-inflammatory microorganisms of the intestine due to the development of specific unfavorable environmental conditions ii) a gradual increase of metabolic activity in and/or in the number of anti-inflammatory microorganisms in the intestine due to the daily supply of probiotics and the development of new intestinal environmental conditions and iii) a reinforced protective mucus layer due to the daily supply of polar lipids of the cereals and the added lecithin.

Subsequent to the fermentation process, the probiotic microorganisms do not grow further in the ready-to-use product. Accordingly, the fermented cereal does not serve as a prebiotic compound since it does not stimulate growth of the probiotics in the intestine. The fermented cereal composition may have a pH below 5.5, which mildly stresses and prepares the probiotic microorganisms for upcoming stress conditions, which for instance will follow in the stomach and in the intestine of GI patients. The pre-stress treatment in the production of probiotics is a matter of a fine balance. Most probiotic products are available as freeze or spray dried preparations. Freeze or spray drying is known as being rough and in many cases kills a great deal of the population. The surviving microorganisms may need time for adaptation when presented to a fluid environment. In other words, freeze or spray dried probiotics may not be prepared adequately for robustness to passage of the stomach and/or competing for the colonization of the intestine. However, it may be possible in certain situations to add freeze or spray dried probiotics to the fermented cereal.

The novel treatment described herein may be initiated at any stage of the IBD or IBS course. The treatment should be carried out by following the novel treatment protocol accurately and the duration may vary from one or few weeks to several months. However, prolonged treatment period appears to provide better long term effects. Following a gradual stop in the intake of the ready-to-use product, IBD and IBS patients will usually experience that the symptoms are absent and not reoccurring. However, some symptoms may reoccur usually within months or years. These symptoms may be treated by entering a maintenance treatment just by following the novel treatment protocol for a shorter duration, which may be of one or more weeks. Also, IBD and IBS patients may acquire experience telling that symptoms may turn up under specific circumstances for instance at specific times at the year, under certain stress conditions or associated to diets in certain communities. In such cases, patients may benefit from entering a maintenance treatment before meeting the specific circumstances. The duration of this maintenance treatment may also be relatively short e.g. one or more weeks.

In the novel treatment both milk, milk components and easily fermentable sugars are omitted in the ready-to-use product and avoided in the diet to create an even more unfavourable environment for microbial growth or life maintenance in the GI tract. Foods that contain relatively large amounts of sugar and/or milk components should be avoided. The foods cover sugar, soft drinks (containing sugar), juice, syrups, candy, cakes, cookies, dried fruit, muesli and other breakfast product with added sugar, ice cream, milk, cream, fermented milks, butter, etc. The patients are recommended to take a supplement of calcium since milk and milk components should be avoided in the treatment. However, many calcium tabs contain relatively large amounts of lactose. Therefore, calcium tabs without lactose should be administered. This is an example of unexpected added components in supplement and foods, which the patients must pay attention to. Foods containing traces of milk or milk components and/or very small amounts of added sugar may be accepted in the diet when following the novel treatment concept. However, no exact limits may be stated for the concentration of added milk, milk components and/or sugar in the foods due to the complexity of different foods and each individual food intake.

The terms "novel treatment", "novel treatment strategy" and "novel treatment concept" refer to the treatment of IBD, IBD-related diseases or IBS.

The following examples are intended to illustrate the present invention and should in no way limit the invention as defined in the claims.

EXAMPLES

Example 1

A 66 years old man was suffering from abdominal pain and diarrhea. He was examined by a physician who could not set up an accurate diagnosis. The patient was consequently redirected to a department of gastroenterology at the local hospital. In the meantime, the symptoms were getting worse and at this time the patient lost more than 2 kg in weight per week. The patient underwent a colonoscopy. No signs of ulcers or necrosis were detected in the lower intestine and the colon. The most likely diagnosis was IBS. Following, the patient was redirected to a local gastroenterologist. On top of the described symptoms, occasional paralysis in the patient's legs began to show up.

The patient undertook a treatment based on a protocol that uses probiotics for the treatment of IBS including abdominal pain and diarrhea disclosed in WO96/29083 and in the scientific literature (Niedzielin et al. 2001 Eur J Gastro-enterol Hepatol. 13:1143-7). Instead of the described 200 ml fruit drink containing $5 \times 10^7$ probiotic bacteria per mL and a minor amount of oat gruel proscribed to be administered twice each day for four weeks to treat gastro-intestinal diseases, the patient took twice a day 10 mL of a similar product containing $10^9$ cfu/ml of *Lactobacillus plantarum* 299v in an oat gruel without added fruit. This amount was chosen to match the number of cfu in Niedzielin et al. 2001. The 10 ml was taken before breakfast and two hours after the last meal in the evening. Having followed this conventional protocol for two weeks, the patient did not experience any positive effect. At that time, the patient had lost more than 30 kg in weight during the three months period from the onset of the disease.

Example 2

Due to the lack of any positive effects from the conventional probiotic treatment, the patient mentioned in Example 1 initiated the novel treatment according to the present invention.

The patient had a daily intake of 500 ml of a fermented oat gruel containing about 90 g fermented oat gruel and $5 \times 10^{11}$ *Lactobacillus plantarum* 299v. This amount of fermented oat gruel and probiotic microorganisms is 50 times higher than proscribed by Niedzielin et al. (2001 Eur J Gastroenterol Hepatol. 13:1143-7) and WO96/29083. The 500 ml fermented product was divided into two portions, which were taken each day before breakfast and as the last meal or drink of the day. The patient experienced a significant reduction of symptoms in less than one week following initiation of the novel treatment. A complete remission was obtained by following the novel treatment for eight weeks. One year later the patient had gained the 30 kg in weight and no relapse has occurred until now, which is about five years subsequent to completion of the novel treatment.

Example 3

A colonoscopy revealed an ulcerative colitis in a 19 years old woman. She was extremely tired and had abdominal pain and bloody diarrheas with more than ten defecations a day. She was hospitalized for 14 days and treated with prednisolon (cortisone) and 5 ASA. This treatment was continued when the patient was sent home. 18 weeks later the tiredness and abdominal pain were still present. The diarrhea was also present but the number of defecations per day was reduced to an average of five. Blood was still present in the stools. The patient experienced severe side effects from the prednisolon including a reduced immune status resulting in continuous infections. She then decided to finish the intake of prednisolon by a gradual reduction. The intake of 5 ASA was continued.

One week following the termination of prednisolon intake, the patient started to follow the novel treatment taking 250 ml of a fermented oat gruel containing *Lactobacillus plantarum* 299v twice a day as described in Example 2. The intake of 5 ASA was continued in parallel for 12 weeks. One week after the treatment start, blood was absent from the stools. On day No. 4 in the novel treatment, the patient's tiredness disappeared. In the following three weeks, the number of defecations varied from two to four. Abdominal pain occurred occasionally during the first three weeks in the novel treatment. During weeks Nos. 4-16, the number of defecations was one or two. The patient experienced two courses of abdominal pain during this period. These were characterized as short pain courses similar to uncomplicated incidents experienced by the patient in the childhood. The treatment was stopped 16 weeks after initiation by a gradual reduction in the daily intake of the fermented oat gruel containing probiotics.

The patient had no UC symptoms throughout the following three and a half year. Subsequently, however, a relapse occurred with a relatively mild diarrhea. The patient then followed the novel treatment protocol for another three weeks resulting in a remission that has continued since, which is 18 months after completion of the second course of the novel treatment.

Example 4

Treatment of IBD Patients Using the Novel Concept for the Treatment of IBD and IBS A series of treatments was set up during a period of four and a half years subsequent to the successful treatment of the 19 years old UC patient as described in Example No. 3. Additional nine UC or CD patients were enrolled to follow the novel treatment concept as described in Example 3. Data, results and comments from the treatments are given in Table 1.

TABLE 1

Data, results and comments concerning nine IBD patients enrolled for the novel treatment concept

| Sex and age (years) | Diagnosis* | Treatment period (weeks) | Result | Comments |
|---|---|---|---|---|
| Male, 20 | CD, moderate | Two | Partial remission | The patient stopped the treatment twice after two weeks in each course when the symptoms disappeared |
| Female, 26 | UC, moderate | 14 | Remission | Subsequently, the patient has once a year - for two years - followed a maintenance treatment for three weeks. |
| Female 16 | UC, moderate | 16 | Remission | |
| Female, 35 | UC, moderate | Eight | Remission | |
| Female, 17 | CD, moderate | One | Positive response | Drop out |
| Female, 45 | UC, mild | Three | Remission | |
| Female, 16 | UC, severe | One | Positive response | Bleeding stopped and diarrhea significantly reduced during the one week treatment. Then drop out |
| Male, 12 | UC, severe | 14 | Remission | |
| Female, 35 | UC, moderate | 14 | Remission | |

*UC: Ulcerative colitis;
CD: Crohn's disease. The stage of the disease was judged prior to treatment start and stated as mild (about 3 or below in SCCAI (SCCAI = Simple Colitis Clinical Activity Index, Jowett et al. 2003 Scand J Gastroenterol. 38: 164-71), moderate (about 4-7 in SCCAI) or severe (about 8 or more in SCCAI).

All patients had been in treatment with conventional medicines such as 5 ASA and/or corticosteroids for more than one year prior to the start of the novel treatment. During the treatment period most patients continued concomitantly their treatment with the conventional medicines due to ethical reasons. They all responded positively to the novel treatment concept. Remission was achieved in the cases where the patients followed the treatment protocol accurately. The results strongly indicate that the novel treatment—with or without combination with conventional medicines—is capable of removing the symptoms from UC and CD patients regardless of the stage of the disease.

Example 5

Treatment of IBS Patients Using the Novel Treatment Concept

Four women with IBS followed the novel treatment protocol for two or three weeks. The first experienced diarrhea and abdominal pain while the three had relatively mild or moderate diarrheas. Data and results from the treatments are given in Table 2.

TABLE 2

Data and results concerning four female IBS patients that followed the novel treatment concept

| Sex and age (years) | Diagnosis | Treatment period (weeks) | Result |
|---|---|---|---|
| Female, 20 | IBS | Three | Remission |
| Female, 47 | IBS | Three | Remission |
| Female, 49 | IBS | Two | Remission |
| Female, 72 | IBS | Three | Remission |

The treated patients all achieved remission. Despite the limited number of patient, the results strongly indicate that the novel treatment concept is capable of turning IBS into remission.

Example 6

Maintenance Treatment of IBS and IBD Patients Using the Novel Treatment Concept

Three women who had previously completed a successful treatment of either UC (Table 1) or IBS(Table 2) followed the treatment protocol for maintenance reasons. Data, results and comments from the treatments are shown in Table 3.

TABLE 3

Data, results and comments concerning three female patients that followed the novel treatment concept for maintenance

| Sex and age (years) | Diagnosis | Treatment period (weeks) | Result | Comments |
|---|---|---|---|---|
| Female, 19 | UC, medium | 2 × three | No UC symptoms | The patient has once a year - for two years - followed the maintenance treatment for three weeks. |
| Female, 47 | IBS | >20 | No IBS symptoms | Previously experienced symptoms have not been present since initiation of the maintenance treatment |
| Female, 72 | IBS | >20 | No IBS symptoms | Previously experienced symptoms have not been present since initiation of the maintenance treatment |

The three women have not experienced any symptom from their UC or IBS since the initiation of the maintenance treatment. The results strongly indicate that the novel treatment concept is efficient in the maintenance treatment of UC and GI disorders despite the low number of patients Example 7

Description of a RCT Study on Patients Suffering from Ulcerative Colitis Using the Novel Concept for the Treatment of IBD and IBS In order to supplement the results described in the previous examples, a randomized clinical trial (RCT) is planned. A Phase IIa, double blinded placebo RCT study will be performed on UC or CD patients essentially as described by for instance by Stremmel et al. 2005 Gut, 54: 966-971. The novel treatment protocol will include the use of fermented oat gruel, which has been fermented with and contains L. plantarum 299v and/or similar probiotic bacteria. The amount of intake in the morning and the evening may be fixed at for instance 250 ml fermented oat gruel containing $10^9$ cfu/ml. The placebo may be cellulose beads in a water solution in which the pH has been adjusted to about 5 with lactic acid and/or acetic acid to mimic the active product, or any other appropriate placebo means. The trial may for instance run for a period between three and 20 weeks depending on the stage of the enrolled UC or CD patients. One expected end point could be remission of at least 50% of the patients to SSCAI values <4 (Jowett et al. 2003 Scand J. Gastroenterol. 38:164-71) within eight to 14 weeks.

Example 8

The Manufacture of a Ready-to-Use Product Consisting of Fermented Oat Gruel with Probiotic Intestine Colonizing *Lactobacillus Plantarum*

The manufacture of a ready-to-use product consisting of fermented oat gruel with probiotic intestine colonizing *Lactobacillus plantarum* is divided into two steps according to this recipe. This first step covers the preparation of oat gruel. This step may be performed essentially as disclosed in EP 415941. An alternative method is to mix 18.5% (w/w) oatmeal and 0.9-2.5% (w/w) malted barley flour with water. The mixture is slowly stirred and heated for 10-20 minutes at 37° C. and following 15-30 minutes at 90-100° C. The resulting oat gruel is cooled to a temperature of about 37° C. and is now ready for the second step namely the fermentation process. A starter culture consisting of *Lactobacillus plantarum* 299 or strain 299v is added to the oat gruel to initiate the fermentation. The amount of added starter culture with a cfu number of about $10^9$/ml is 0.01, 0.1 or 1.0% (v/v). The fermentation is carried out with mild stirring at 37° C. for 12-24 hrs. The resulting ready to use product with a cfu number of about $10^9$/ml and pH below 5 is then cooled at 4° C. and packed for instance in sterile storage containers of 250 ml, which have a shelf life of at least two months when kept at 4° C.

Example 9

The Manufacture of a Ready-to-Use Product Consisting of Fermented Oat Gruel with Probiotic Microorganisms and Lecithin A ready to use product consisting of fermented oat gruel with probiotic microorganisms is manufactured as described in Example 8. Subsequently, lecithin is added. 12 grams of granulated lecithin such as "Lecithin Granulat" from Biosym A/S, DK-7430 Ikast, Denmark, are added per liter fermented oat gruel with probiotic microorganisms. The mixture is stirred for about one minute and kept overnight at 4° C. resulting in a new ready-to-use product consisting of fermented oat gruel with probiotic microorganisms and lecithin with a cfu number of about $10^9$/ml and pH below 5. This product is packed for instance in sterile storage containers of 250 ml, which have a shelf life of at least two months when kept at 4° C.

More or less amounts of lecithin and other physical forms and qualities of lecithin can be used in this protocol. Numerous commercial lecithins are available and most with different contents of phosphatidylcholine, lysophosphatidylcholine, phosphatidylinositol and phosphatidylethanolamine. The fatty acids residues of these phospholipids may be saturated, mono-unsaturated or poly-unsaturated. Also, the lecithin to be used in this protocol may have different physical forms such as liquid, granulated, encapsulated or mixed with any other substances such as vegetable oils. Encapsulated lecithin include formulations where lecithin is designed to be released at specific locations in the gastrointestinal tract for instance as defined as "retarded release" by Stremmel et al. 2005 Gut 54:966-971.

Example 10

The Manufacture of a Ready-to-Use Product Consisting of Fermented Oat Gruel and Microorganisms Capable of Fermenting Oat Gruel A protocol for the manufacture of a ready to use product consisting of fermented oat gruel with probiotic intestine colonizing *Lactobacillus plantarum* is described in Example 8. An alternative ready to use product consisting of fermented oat gruel with other microorganisms capable of fermenting oat gruel can be manufactured using the following protocol.

Bacteria are isolated as starter culture candidates from intestinal mucosa biopsies of healthy human volunteers that have been on a one week diet with a daily intake of at least 25 g oatmeal. The isolation and growth of the bacteria are essentially carried out as described for intestinal bacteria of horses in U.S. Pat. No. 6,537,544. A set of 20 strains belonging to the group consisting of Lactic Acid Bacteria, non-pathogenic *Streptococcus* spp, *Pediococcus* spp, *Bifidobacterium* spp. and *Propionibacterium* spp. is selected for an analysis of fermentation performance. 20 samples of 500 ml oatmeal gruel prepared as described in Example 8 are each inoculated with a pure culture of one single strain from the set to an initial cfu number of about $10^5$. The inoculated samples are mildly stirred at 37° C. for 24 hrs. Following, the pH is measured and the cfu numbers determined in each sample. The bacterial strains giving rise to cfu numbers at about $10^9$ or above and pH below 5 in the fermented product are termed "oatmeal starter strains". Previously described cereal starter cultures such as in WO9117672 are also included in "oatmeal starter strains".

The manufacture of a ready to use product consisting of fermented oat gruel with microorganisms capable of fermenting oat gruel is essentially carried out as described in Example 8 except for the use of the specific starter culture. Here, the starter culture is consisting of one or more of the "oatmeal starter strains" instead of *Lactobacillus plantarum* 299 or strain 299v. The amount of the "oatmeal starter strains" with a cfu number of about $10^9$/ml is 0.01, 0.1 or 1.0% (v/v). The resulting ready to use product with a cfu number of about $10^9$/ml and pH below 5 is cooled at 4° C. and packed for instance in sterile storage containers of 250 ml. The shelf life is at least two months when kept at 4° C.

Example 11

The Manufacture of a Ready-to-Use Product Consisting of Fermented Oat Gruel and a Variety of Microorganisms As described, the fermented oat gruel contains two effectors for combating IBD and IBS namely fermented oat and probiotic microorganisms. Both effectors are present following fermentation of the oat gruel as described in the previous examples. However, additional microorganisms from other sources may be added subsequent to the oat fermentation. The added microbial strains may be a strong effector in the intestine of IBD or IBS patients but incapable of fermenting oats or competing with oat fermenting strains.

A number of *Bifidobacterium* strains (and strains from other bacterial species) have been shown to exert positive effects in IBD or IBS patients (refs). However, these strains are not expected to be capable of performing an effective fermentation in oats. Therefore, the *Bifidobacterium* strains are grown in a conventional growth medium such as MRS (ref) possibly with added inulin-oligofructose (Furrie et al. 2005 Gut 54:1346). The *Bifidobacterium* strains are grown at optimal growth conditions. Subsequent to the end of growth, lactic acid is added to the medium at a final concentration of 0.8% to make the bacteria adapt to an acidic environment. Following two hours in the medium containing lactic acid the bacteria are harvested by centrifugation at 5000 rpm for 10 minutes. The bacteria are resuspended in 1/100 of the growth medium containing lactic acid resulting in a suspension containing about $10^{12}$ cfu/ml. The suspension is termed "extra microorganisms".

Fermented oat gruel with probiotic intestine colonizing *Lactobacillus plantarum* and *Bifidobacterium* strain(s) may be manufactured using the procedure described in Example 8 followed by the addition of "extra microorganisms". An amount corresponding to 0.1% (v/v) of "extra microorganisms" is added to the product consisting of fermented oat gruel with probiotic intestine colonizing *Lactobacillus plantarum* if the ready to use product shall contain equal amounts of *Lactobacillus* and *Bifidobacterium*. The ready to use product is packed for instance in sterile storage containers of 250 ml, which have a shelf life of at least two months when kept at 4° C.

If a ready to use fermented oat product should be preferred containing essentially no living oat fermenting bacteria, the product consisting of fermented oat gruel with probiotic intestine colonizing *Lactobacillus plantarum* must be stirred and heated at 100° C. for about 30 minutes before cooling at 4° C. and the subsequent addition of "extra microorganisms".

Example 12

The Manufacture of a Ready to Use Product Consisting of Fermented Maize-Sorghum and Microorganisms Capable of Fermenting Maize and Sorghum Togwa is a fermented cereal gruel consisting of a mixture of maize and sorghum including microorganisms capable of fermenting these cereals (Mugula et al. 2003 Int J Food Microbiol. 83:307-18). A maize-sorghum gruel is prepared by mixing 10-20% (w/w) maize and sorghum flour with water. The mixture is stirred and heated for about 10-15 minutes at 90-100° C. followed by cooling to a temperature of about 37° C. A starter culture with a cfu number of about $10^7$-$10^9$/ml is added in the amount of 0.01, 0.1 or 1.0% (v/v). The starter culture may be produced as described in Example 10 except that 20 samples of 500 ml maize-sorghum gruel are inoculated with a pure culture of one single strain to an initial cfu number of about $10^5$. The bacterial strains giving rise to cfu numbers at least $10^8$ and pH below 5 in the fermented maize-sorghum gruel are termed "togwa starter strains". Following the addition of "togwa starter strains" to the maize-sorghum gruel the fermentation is carried out with mild stirring at 37° C. for 12-24 hrs. The resulting ready to use product with a cfu number of about $10^8$-$10^8$/ml and pH below 5 is then cooled at 4° C. and packed for instance in sterile storage containers of 250 ml. The shelf life is at least two months when kept at 4° C. It should be noted that traditional Togwa may contain yeast strains as well as bacteria.

Example 13

Treatment of UC Patients with a Ready to Use Product Consisting of Fermented Oat Gruel with Probiotic Microorganisms and Added Lecithin Leads to a Faster and/or a More Stable Reduction in the Symptoms Level Two female UC patients of the age of 46 and 55 years with an initial SCCAI score of 6 and 4, respectively, initiated the novel treatment as described in Examples 3 and 4. However, the daily intake used in this treatment was a 500 ml ready-to-use product containing about 90 g fermented oat gruel, $5 \times 10^{11}$ Lactobacillus plantarum 299v and 6 g added lecithin with about 23% PC and 19% PI. The 500 ml ready-to-use product was divided into two portions, which were taken each day before breakfast and as the last meal or drink of the day. The UC symptoms of the 46 years old woman were gradually reduced and remission was obtained within the first 14 days following treatment start. The state of remission was maintained throughout the treatment period.

The UC symptoms of the 55 years old woman fluctuated between a SCCAI score of 4 and 1 during the first six weeks. However, remission was obtained during the remaining treatment period except for two days where the patient experienced a traveller's diarrhoea during a visit to Thailand.

These results show a much faster and/or a more stable reduction in the symptoms levels during the treatment course compared to patients that have been treated with the similar product without added lecithin. The much faster and more stable reduction of UC symptoms for the 46 years old woman was observed already during the first two weeks following the treatment onset.

The 55 years old woman in the study showed fluctuating symptom levels during the first six weeks of the treatment course, which was in accordance with patients treated with the ready to use product without added lecithin. In contrast, however, the subsequent state of remission was maintained without relapse throughout the treatment period.

Example 14

A UC Patient Experienced a Faster and More Stable Reduction in UC Symptoms when Treated with a Ready to Use Product Consisting of Fermented Oat Gruel with Probiotic Microorganisms and Added Lecithin Compared to the Similar Treatment with a Ready to Use Product without Lecithin A 33 years old woman with a severe UC was treated for 10 weeks with a daily intake of 500 ml of a ready-to-use product containing about 90 g fermented oat gruel and $5 \times 10^{11}$ Lactobacillus plantarum 299v. The 500 ml ready-to-use product was divided into two portions, which were taken each day before breakfast and as the last meal or drink of the day. During the 10 weeks treatment the symptoms were gradually reduced from initially SCCAI about 8 to about 2-4. However, the fluctuations in the symptoms level were significant during the treatment course, which have been observed for several patients that have followed the treatment with the ready to use product without lecithin. The 33 years old UC patient stopped the treatment in week no. 10 due to a fortnight trip overseas. Accordingly, the termination of the treatment was about one month earlier than recommended and too early because of the unstable level of symptoms. During the trip the patient experienced a complete relapse resulting in a SCCAI of about 8. She then initiated a new treatment course but now with a 500 ml ready-to-use product containing about 90 g fermented oat gruel, $5 \times 10^{11}$ Lactobacillus plantarum 299v and 6 g added lecithin with about 23% PC and 19% PI. The 500 ml ready-to-use product with added lecithin was divided into two portions, which were taken each day before breakfast and as the last meal or drink of the day. At the end of the first week of the treatment course with the ready to use product with added lecithin, the symptoms level was reduced from SCCAI of about 8 to about 4 and during the following two weeks the SCCAI level was constantly at 3-4. During the following three weeks the symptoms level was gradually reduced and remission obtained during the remaining eight weeks of the treatment period.

This demonstrates that the ready to use product with added lecithin exerted a faster and more stable reduction in the symptoms level compared to the ready to use products without added lecithin.

Example 15

Taste and Consistency of the Ready to Use Product Containing Lecithin

A ready to use product consisting of fermented oat gruel with probiotic microorganisms and added lecithin was manufactured as described in Example 9. The product was expected to possess an unpleasant greasy constitution and "fatty" taste compared to the ready to use product without added lecithin. However, the ready to use product with added lecithin surprisingly showed a much better taste and a comfortable mouth feeling. The taste was round and free of the acidic and bitter aftertaste that is a feature to the ready to use product without added lecithin. Also, the mouth feeling was experienced as nice and smooth as opposed to the ready to use product without added lecithin. Four test persons declared independently that the aroma and rheology of the ready to use product with added lecithin is much more delicious than the ready to use product without lecithin. This is important to patient compliance since the ready to use product shall be administered orally in relatively large amounts for long periods.

The invention claimed is:

1. A method of treating irritable bowel syndrome (IBS) in a human subject, the method comprising administering to the subject a fermented cereal comprising Lactobacillus plantarum cells of strain 299 or 299v, wherein the fermented cereal is administered in an amount providing at least 18 g (dry weight) of a fermented cereal and at least $1 \times 10^{11}$ cfu of said Lactobacillus plantarum cells on a daily basis, and wherein the fermented cereal is administered for a period of time effective to reduce at least one symptom of IBS.

2. The method of claim 1, wherein the treatment induces remission.

3. The method of claim 1, wherein the treatment provides maintenance of the disease.

4. The method of claim 1, wherein the cereal is fermented by said Lactobacillus plantarum cells.

5. The method of claim 1, wherein said Lactobacillus plantarum cells are added to the fermented cereal.

6. The method of claim 1, where the cereal that is fermented is selected from barley, corn, millet, oats or oatmeal, quinoa, rice, rye, sorghum, triticale, wheat, and cassava.

7. The method of claim 1, wherein the cereal that is fermented is oats or oatmeal.

8. The method of claim 1, wherein the fermented cereal is administered in an amount providing at least $2 \times 10^{11}$ cfu of said *Lactobacillus plantarum* cells on a daily basis.

9. The method of claim 1, wherein the fermented cereal is administered in an amount providing at least $5 \times 10^{11}$ cfu of said *Lactobacillus plantarum* cells on a daily basis.

10. The method of claim 1, wherein the fermented cereal is administered in an amount providing at least 36 g (dry weight) of fermented cereal on a daily basis.

11. The method of claim 1, wherein the fermented cereal is administered in an amount providing at least 90 g (dry weight) of fermented cereal on a daily basis.

12. The method of claim 1, wherein the fermented cereal comprises at least $1 \times 10^8$ cfu/ml of said *Lactobacillus plantarum* cells.

13. The method of claim 1, wherein the fermented cereal comprises at least $1 \times 10^9$ cfu/ml of said *Lactobacillus plantarum* cells.

14. The method of claim 1, wherein the fermented cereal comprises at least 0.05 g/ml (dry weight) of fermented cereal.

15. The method of claim 1, wherein the fermented cereal comprises at least 0.1 g/ml (dry weight) fermented cereal.

16. The method of claim 1, wherein the fermented cereal comprises at least 0.18 g/ml (dry weight) fermented cereal.

17. The method of claim 1, wherein the fermented cereal comprises added lecithin or added phosphatidylcholine and is orally administered.

18. The method of claim 17, wherein the fermented cereal is administered in an amount providing at least 0.1 g added lecithin or phosphatidylcholine on a daily basis.

19. The method of claim 17, wherein the fermented cereal is administered in an amount providing at least 0.5 g added lecithin or phosphatidylcholine on a daily basis.

20. The method of claim 17, wherein the fermented cereal is administered in an amount providing at least 1 g added lecithin or phosphatidylcholine on a daily basis.

21. The method of claim 1, wherein the fermented cereal further comprises one or more food additives, medical additives, taste enhancers, food colors, pH or osmosis regulators, vitamins, herbs, herbal components, minerals, viscosity regulators, lipids, emulsifiers, glutamine or other amino acids, antioxidants, blood pressure regulators, or pain relief substances.

22. The method of claim 1, wherein the fermented cereal further comprises an additional active agent suitable for treatment of gastrointestinal disorders.

23. The method of claim 1, wherein the fermented cereal is administered in the form of a drinkable, eatable, anally administrable, or tube administrable product.

24. The method of claim 1, wherein the fermented cereal comprises fermented oats, lactic acid bacteria, and added lecithin or phosphatidylcholine and is orally administered.

25. The method of claim 1, wherein said at least one symptom of IBS is selected from the group consisting of noncardiac chest pain, nonulcer dyspepsia, chronic constipation or diarrhea, and abdominal pain.

* * * * *